(12) United States Patent
Schmidt-Forst

(10) Patent No.: US 8,827,974 B2
(45) Date of Patent: Sep. 9, 2014

(54) ABSORBENT TAMPON FOR FEMININE HYGIENE

(75) Inventor: Alexander M. Schmidt-Forst, Erlangen (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 358 days.

(21) Appl. No.: 11/322,780

(22) Filed: Dec. 30, 2005

(65) Prior Publication Data
US 2007/0260211 A1 Nov. 8, 2007

(51) Int. Cl.
*A61F 13/20* (2006.01)
*A61F 13/15* (2006.01)

(52) U.S. Cl.
CPC ......... *A61F 13/2068* (2013.01); *A61F 13/2085* (2013.01); *A61F 13/206* (2013.01); *A61F 13/20* (2013.01); *A61F 13/202* (2013.01); *A61F 13/2088* (2013.01); *A61F 13/2094* (2013.01); *A61F 2013/15422* (2013.01); *Y10S 604/904* (2013.01)
USPC . 604/385.17; 604/904; 604/379; 604/385.18; 604/377; 604/370; 604/904

(58) Field of Classification Search
CPC . Y10S 604/904; A61F 13/26; A61F 13/2085; A61F 13/206; A61F 13/2068; A61F 13/20; A61F 2013/15422; A61F 13/202; A61F 13/2088; A61F 13/2094
USPC ........... 604/11, 14, 15, 16, 18, 904; D24/141; 28/118, 119, 120
See application file for complete search history.

(56) References Cited

U.S. PATENT DOCUMENTS

| | | | |
|---|---|---|---|
| 1,887,526 | A | 11/1932 | Spielberg et al. |
| 2,123,750 | A | 7/1938 | Schulz |
| 2,386,590 | A | 10/1945 | Calhoun |

(Continued)

FOREIGN PATENT DOCUMENTS

| | | | |
|---|---|---|---|
| EP | 0 108 637 | A2 | 5/1984 |
| EP | 0 149 155 | A2 | 7/1985 |

(Continued)

OTHER PUBLICATIONS

Hegde, Raghavendra et al. "Rayon Fibers." Apr. 2004. http://www.engr.utk.edu/mse/Textiles/Rayon%20fibers.htm Accessed Wednesday, Aug. 29, 2012.*

(Continued)

*Primary Examiner* — Adam Marcetich
(74) *Attorney, Agent, or Firm* — Kimberly Clark Worldwide, Inc.

(57) ABSTRACT

The present invention provides an absorbent tampon having a mass of an absorbent composite compressed into a generally cylindrical shape. The absorbent composite used in the tampon of the present invention has at least a first layer and a second layer wherein the second layer is adjacent the first layer. The first layer is prepared from a first absorbent material having a first physical property and the second layer is prepared from a second absorbent material having a second physical property, wherein the first physical property is the same physical property as the second physical property, but the value of the second physical property is different from the first physical property. By providing layers in the absorbent composite different physical properties, the tampons of the present invention can have different properties at various locations of the tampon to provide a tampon having desirable features, such as improve leakage protection.

7 Claims, 4 Drawing Sheets

(56) References Cited

U.S. PATENT DOCUMENTS

| | | | | |
|---|---|---|---|---|
| 2,499,414 | A | 3/1950 | Rabell | |
| 2,926,394 | A | 3/1960 | Bletzinger et al. | |
| 3,068,867 | A | 12/1962 | Bletzinger et al. | |
| 3,572,341 | A * | 3/1971 | Glassman | 604/359 |
| 3,628,534 | A * | 12/1971 | Donohue | 604/366 |
| 3,670,731 | A * | 6/1972 | Harmon | 604/368 |
| 3,710,793 | A * | 1/1973 | Glassman | 604/359 |
| 3,731,687 | A * | 5/1973 | Glassman | 604/379 |
| 3,732,866 | A * | 5/1973 | Accavallo | 604/379 |
| 3,738,364 | A | 6/1973 | Brien et al. | |
| 3,854,481 | A * | 12/1974 | Messing | 604/380 |
| 3,946,737 | A | 3/1976 | Kobler | |
| 4,109,354 | A | 8/1978 | Ronc | |
| 4,200,101 | A * | 4/1980 | Glassman | 604/385.18 |
| 4,217,900 | A | 8/1980 | Wiegner et al. | |
| 4,335,720 | A | 6/1982 | Glassman | |
| 4,543,098 | A * | 9/1985 | Wolfe et al. | 604/370 |
| 4,573,988 | A * | 3/1986 | Pieniak et al. | 604/379 |
| 4,661,101 | A | 4/1987 | Sustmann | |
| 4,787,699 | A | 11/1988 | Moulin | |
| 4,787,895 | A | 11/1988 | Stokes et al. | |
| 4,816,100 | A | 3/1989 | Friese | |
| 4,859,273 | A | 8/1989 | Friese | |
| 4,863,450 | A | 9/1989 | Friese | |
| 4,979,947 | A | 12/1990 | Berman | |
| 5,185,010 | A * | 2/1993 | Brown, Jr. | 604/379 |
| 5,300,054 | A | 4/1994 | Feist et al. | |
| 5,366,450 | A * | 11/1994 | DeGroot | 604/366 |
| 5,439,458 | A | 8/1995 | Noel et al. | |
| 5,486,167 | A | 1/1996 | Dragoo et al. | |
| 5,505,719 | A | 4/1996 | Cohen et al. | |
| 5,525,407 | A | 6/1996 | Yang | |
| 5,533,990 | A | 7/1996 | Yeo | |
| 5,569,226 | A | 10/1996 | Cohen et al. | |
| 5,592,725 | A | 1/1997 | Brinker | |
| 5,607,414 | A | 3/1997 | Richards et al. | |
| 5,681,300 | A | 10/1997 | Ahr et al. | |
| 5,686,034 | A | 11/1997 | Frankham et al. | |
| 5,755,906 | A | 5/1998 | Achter et al. | |
| 5,772,645 | A | 6/1998 | Zadini et al. | |
| 5,832,576 | A | 11/1998 | Leutwyler et al. | |
| 5,849,000 | A * | 12/1998 | Anjur et al. | 604/367 |
| 5,911,712 | A | 6/1999 | Leutwyler et al. | |
| 6,039,716 | A | 3/2000 | Jessup et al. | |
| 6,039,828 | A * | 3/2000 | Achter et al. | 156/217 |
| 6,056,714 | A | 5/2000 | McNelis et al. | |
| 6,183,457 | B1 | 2/2001 | Kuhn | |
| 6,186,994 | B1 * | 2/2001 | Bowles et al. | 604/385.17 |
| 6,186,995 | B1 * | 2/2001 | Tharpe, Jr. | 604/385.18 |
| 6,283,952 | B1 | 9/2001 | Child et al. | |
| 6,302,862 | B1 * | 10/2001 | Osborn et al. | 604/15 |
| 6,310,269 | B1 | 10/2001 | Friese et al. | |
| 6,415,484 | B1 * | 7/2002 | Moser | 28/118 |
| 6,554,814 | B1 * | 4/2003 | Agyapong et al. | 604/385.18 |
| 6,599,521 | B1 | 7/2003 | Resheski Wedepohl et al. | |
| 6,682,513 | B2 | 1/2004 | Agyapong et al. | |
| 6,710,220 | B2 * | 3/2004 | Kluger et al. | 604/360 |
| 6,889,409 | B2 | 5/2005 | Friese et al. | |
| 7,138,559 | B2 * | 11/2006 | Kluger et al. | 604/360 |
| 2002/0107494 | A1 * | 8/2002 | Williams | 604/361 |
| 2002/0120246 | A1 * | 8/2002 | Buzot | 604/385.17 |
| 2002/0156343 | A1 * | 10/2002 | Zunker | 600/30 |
| 2003/0023214 | A1 | 1/2003 | DiSalvo et al. | |
| 2003/0176844 | A1 | 9/2003 | Randall et al. | |
| 2003/0208180 | A1 * | 11/2003 | Fuchs et al. | 604/385.17 |
| 2003/0229328 | A1 | 12/2003 | Costa | |
| 2005/0143708 | A1 * | 6/2005 | Hagberg et al. | 604/385.18 |
| 2005/0277904 | A1 * | 12/2005 | Chase et al. | 604/385.18 |
| 2005/0283128 | A1 * | 12/2005 | Chase et al. | 604/378 |
| 2006/0074391 | A1 * | 4/2006 | Hagberg et al. | 604/385.18 |
| 2006/0247592 | A1 | 11/2006 | Schmidt-Först et al. | |
| 2007/0203429 | A1 * | 8/2007 | Ziv | 600/573 |
| 2007/0266503 | A1 | 11/2007 | Schmidt-Forst et al. | |

FOREIGN PATENT DOCUMENTS

| | | | | |
|---|---|---|---|---|
| EP | 0 163 179 | A1 | 12/1985 | |
| EP | 0 639 363 | B1 | 4/1998 | |
| EP | 0 965 316 | A2 | 12/1999 | |
| EP | 1 064 901 | A2 | 1/2001 | |
| EP | 1064901 | * | 1/2001 | A61F 13/20 |
| EP | 0 685 213 | B1 | 10/2001 | |
| EP | 0 716 170 | B1 | 2/2002 | |
| EP | 0 611 562 | B2 | 1/2003 | |
| EP | 0 422 660 | B2 | 12/2003 | |
| EP | 0 735 848 | B2 | 12/2003 | |
| EP | 1 481 656 | A1 | 12/2004 | |
| GB | 1 409 172 | A | 10/1975 | |
| GB | 2 284 992 | A | 6/1995 | |
| JP | 61-048724 | U1 | 4/1986 | |
| KR | 10-0899047 | B1 | 5/2009 | |
| WO | WO 89/07924 | A1 | 9/1989 | |
| WO | WO 97/23185 | A1 | 7/1997 | |
| WO | WO 98/47456 | A1 | 10/1998 | |
| WO | WO 00/37013 | A1 | 6/2000 | |
| WO | WO 00/59439 | A1 | 10/2000 | |
| WO | WO 00/75427 | A2 | 12/2000 | |
| WO | WO 03/055429 | A1 | 7/2003 | |
| WO | WO 2004/021943 | A1 | 3/2004 | |
| WO | WO 2004/113608 | A2 | 12/2004 | |

OTHER PUBLICATIONS

"Define Gauze at Dictionary.com" entry http://dictionary.reference.com/browse/gauze?r=66. Accessed Feb. 6, 2014.*

* cited by examiner

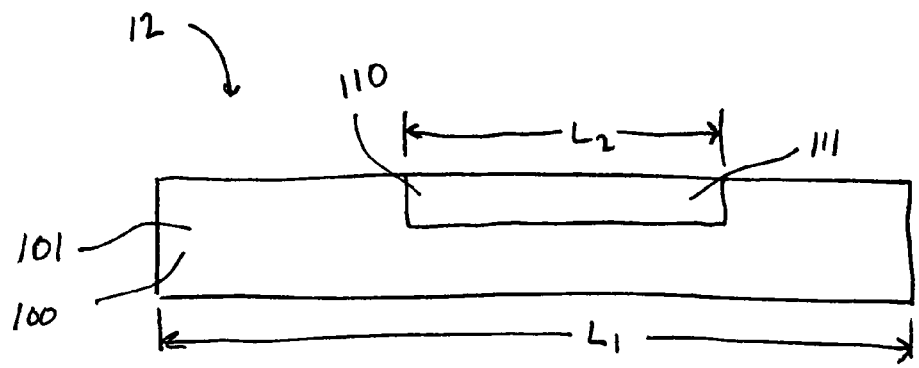
FIG 3
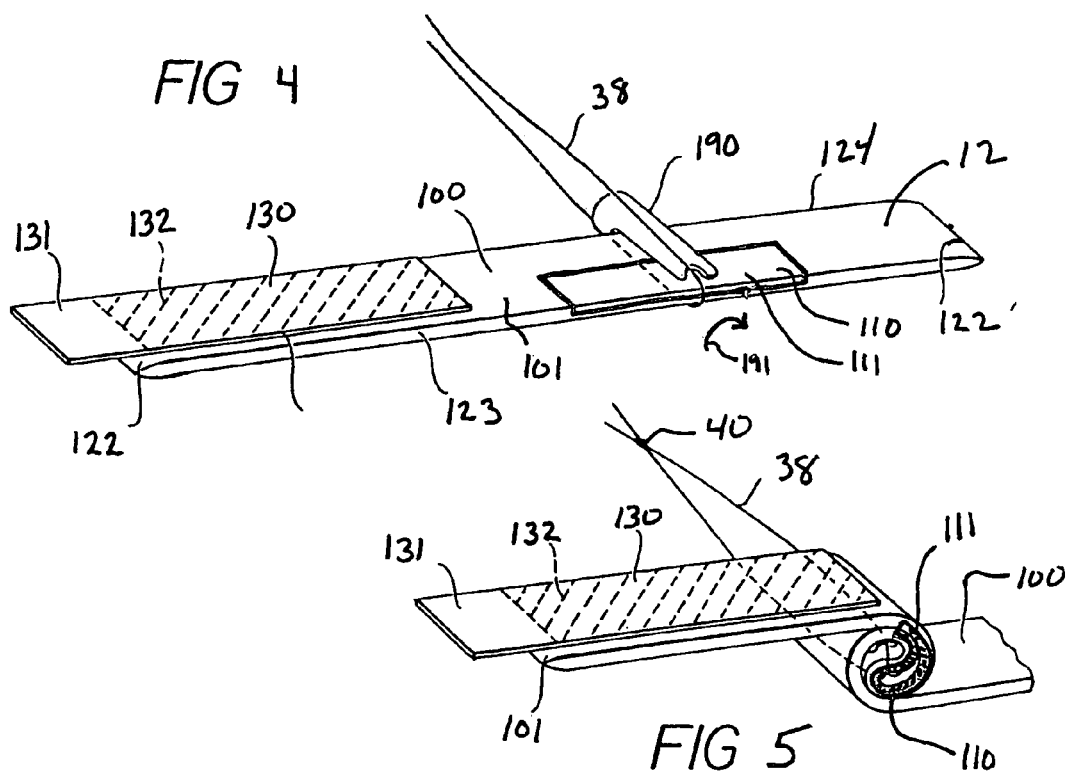
FIG 4
FIG 5

ABSORBENT TAMPON FOR FEMININE HYGIENE

FIELD OF THE INVENTION

The present invention concerns personal hygiene products, more particularly, catamenial tampons.

BACKGROUND OF THE INVENTION

There are two basic types of catamenial tampons used for feminine hygiene currently available on the market. The first type is a digital tampon which is designed to be inserted into a woman's vagina directly by the user's fingers. The second type is a tampon which is designed to be inserted with the aid of an applicator. Both types are usually made by folding or rolling a loosely associated strip of absorbent material into an elongated shape often referred to as a "softwind." The softwind is then radially and/or biaxially compressed into a pledget. The pledget may or may not include a cover which will facilitate holding the absorbent material together once compressed. In both types of tampons, a withdrawal string is attached to the absorbent, either before or after compression, to facilitate removal of the tampon from the user's vagina after it has absorbed a certain quantity of body fluid, such as menses, blood, etc.

It has been found that many tampons, both digital as well as those delivered by an applicator, are often unable to prevent premature leakage of body fluid. Premature leakage can result from a number of factors. For example, one factor is that the tampon does not properly fit above the introital region of the vagina. Another example is that the tampon is not shaped correctly to intercept fluid flow through the vaginal canal. Still another example is that the folds and convolutions of the vagina are not all in contact with the tampon and therefore body fluid is able to bypass the tampon.

While various types of tampons exist in the art, there remains a need for a tampon product that helps better prevent leakage of body fluid soon after being inserted into a woman's vagina and provides utilization of the absorbent during use.

SUMMARY OF THE INVENTION

The present invention provides an absorbent tampon having a mass of an absorbent composite compressed into a generally cylindrical shape. The absorbent composite used in the tampon of the present invention has at least a first layer and a second layer wherein the second layer is adjacent the first layer. The first layer is prepared from a first absorbent material having a first physical property and the second layer is prepared from a second absorbent material having a second physical property, wherein the first physical property is the same physical property as the second physical property, but the value of the second physical property is different from the first physical property. By providing layers in the absorbent composite different physical properties, the tampons of the present invention can have different properties at various locations of the tampon to provide a tampon having desirable features, such as improve leakage protection.

In another embodiment of the present invention, provided is an absorbent tampon prepared from a mass of an absorbent composite compressed into a generally cylindrical shape. In this embodiment of the present invention, the absorbent composite has a first layer and a second layer, wherein the second layer is adjacent the first layer. The first absorbent layer of the absorbent composite has a first length and a first width and the second absorbent layer has a second length and a second width, wherein the first length is greater than the second length. Stated another way the second absorbent layer is shorter than the first absorbent layer. In a further aspect of this embodiment of the present invention, the first width of the first absorbent layer is greater than the second width of the second absorbent layer. In an additional aspect of this embodiment, the second layer is positioned on the first absorbent layer at or near the central region of the first absorbent layer, wherein the central region is located at a position along the first length which is about one-half a distance of the first length of the first absorbent layer.

In another embodiment of the present invention, provided is a method of forming a tampon. In the method of this embodiment of the present invention, a first and second absorbent material is provided, wherein the physical properties of the first absorbent material are different from the second absorbent material. The second absorbent material is placed onto the first absorbent material to form an absorbent composite. The absorbent composite is formed into a softwind having a generally cylindrical shape. The softwind is then compressed to increase the density of the absorbent composite, thereby forming the tampon. In an additional aspect of this embodiment of the present invention, softwind is formed by radially winding the absorbent composite.

In each of the embodiments of the present invention, the tampon may be provided with a withdrawal string to facilitate removal of the tampon from a user's vagina.

BRIEF DESCRIPTION OF THE DRAWINGS

FIG. 3 shows a side view of another alternative absorbent composite used to prepare the tampon of the present invention.

FIG. 4 shows a perspective view of an absorbent composite with an additional cover material used to prepare the tampon of the present invention before the absorbent composite is formed into a softwind.

FIG. 5 shows a perspective view of the formation of the absorbent composite used to prepare the tampon of the present invention in the process of forming a softwind.

DEFINITIONS

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, "disposable" means being disposed of after a single use and not intended to be washed and reused.

As used herein, the term "autogenous bonding", "autogenously bondable" and similar forms of these words, means bonding provided by fusion and/or self-adhesion of fibers and/or filaments without an applied external adhesive or bonding agent. Autogenous bonding can be provided by contact between fibers and/or filaments while at least a portion of the fibers and/or filaments are semi-molten or tacky. Autogenous bonding may also be provided by blending a tackifying resin with the thermoplastic polymers used to form the fibers and/or filaments. Fibers and/or filaments formed from such a blend can be adapted to self-bond with or without the application of pressure and/or heat. Solvents may also be used to cause fusion of fibers and filaments which remain after the solvent is removed.

Figure 2:
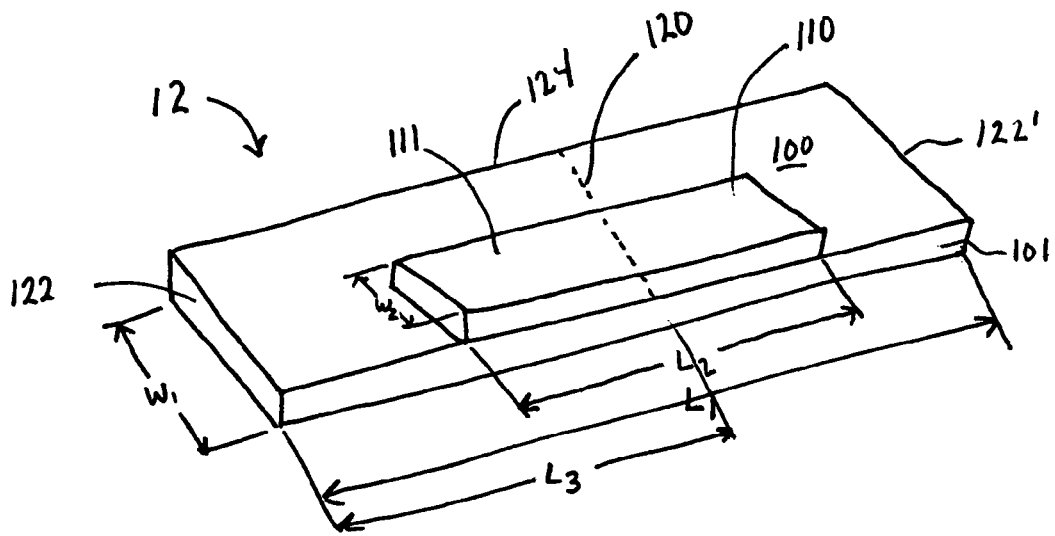
FIG. 2 shows a perspective view of an alternative absorbent composite used to prepare the tampon of the present invention.
Figure 6:
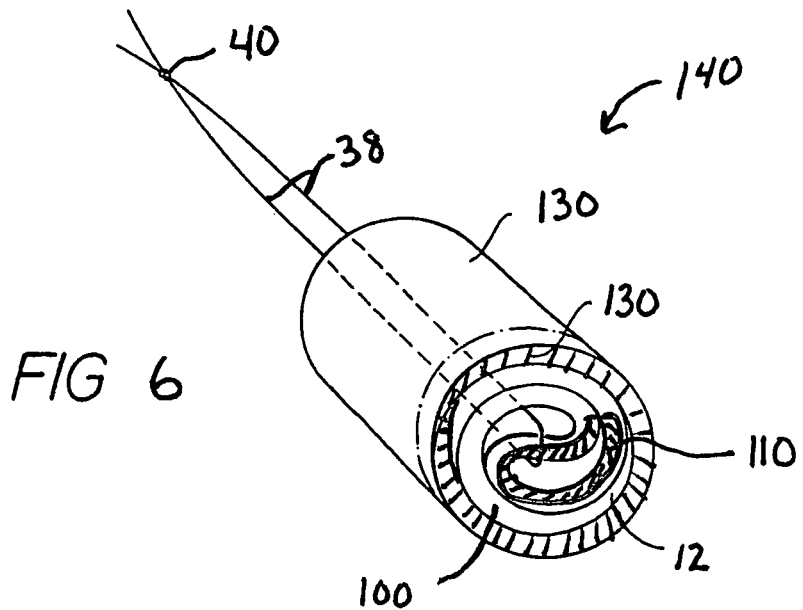
FIG. 6 shows a softwind used to prepare the tampon of a tampon of the present invention.

As used herein, the term "non-cylindrical shape" means a tampon having a second zone of the tampon where the cross-sectional Diameter of the second zone is at least 5% greater than a cross-sectional Diameter of at least a first zone of the tampon, such Diameter of the respective zones being determined according to the Radial Expansion Test herein. Examples not drawn to scale, and rather, slightly exaggerated for illustration purposes, are seen in FIGS. 2, 4 and 6. The at least 5% greater value is believed to readily distinguish the inventive tampons from prior tampons that through manufacturing variability may have had zones with varying Diameters (i.e., none of the prior tampons had first and second zones with Diameters that differed by more than 5%, as well as none of the prior packages of multiple tampons consistently having each tampon in the pack which would have a non-cylindrical shape when the tampon absorbed liquid).

As used herein, the term "cross-section", "cross-sectional" and similar forms of these words, mean the plane which extends laterally through the tampon and which is orthogonal to the longitudinal axis of the tampon.

As used herein, the term "Diameter" and similar forms of this word, means the cross-sectional diameter of the tampon as measured according to the Radial Expansion Test herein.

As used herein the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

DETAILED DESCRIPTION OF THE INVENTION

The tampon of the present invention is designed to be inserted above the introital region of a woman's vagina and is designed to function so as to intercept the fluid flow of menses, blood, and other body fluids and prevent the fluid from exiting the vagina. The tampon of the present invention is prepared from an absorbent composite, which has at least two layers. To obtain a better understanding of the absorbent composite used to prepare the tampon of the present invention, attention is directed to the figures.

Figure 7:
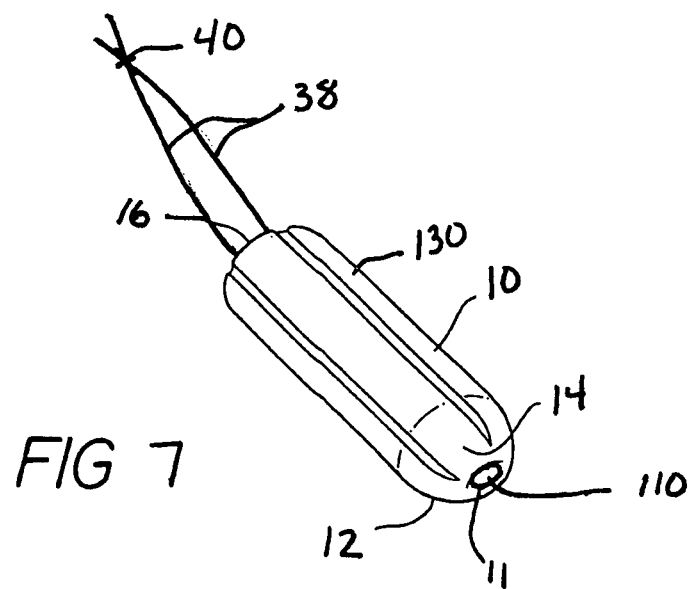
FIG. 7 shows a perspective view of a tampon of the present invention.

As is shown in FIG. 7, the tampon 10 includes a mass of absorbent material 12 compressed into a generally cylindrical shape. Tampon 10 generally has an insertion end 14 and a trailing end 16, wherein the insertion end 14 is designed to be the first part of the tampon which enters the woman's vaginal cavity. While in use, the tampon 10 of the present invention is designed to be entirely positioned within the woman's vagina.

Figure 1:
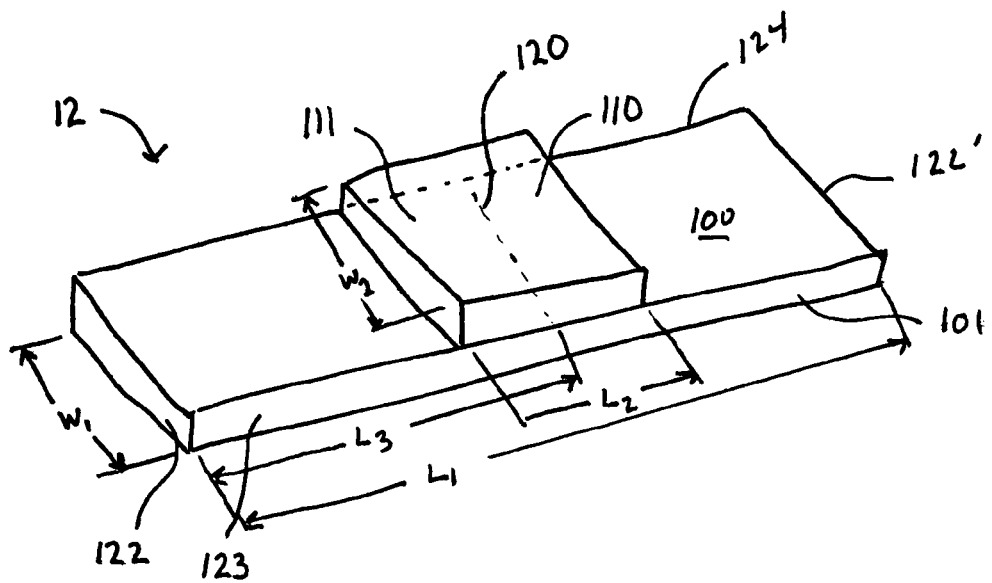
FIG. 1 shows a perspective view of an absorbent composite used to prepare the tampon of the present invention.

As is shown in FIG. 1, the absorbent material 12 is a composite material prepared from a first layer 100 of a first absorbent material 101 and a second layer 110 of a second absorbent material 111. In one embodiment of the present invention, the first absorbent material 101 has a first physical property and the second absorbent material 111 has a second physical property, wherein the first physical property is the same physical property as the second physical property, but the value of the second physical property is different from the value of the first physical property. By providing layers in the absorbent composite 12 with different physical properties, the tampons of the present invention can have different properties at various locations of the tampon to provide a tampon having desirable features, such as improve leakage protection.

Examples of physical properties which each layer of the absorbent composite 12 may have that may be different include for example, density and hydrophilicity. By providing a density gradient, the denser layer of the absorbent composite will have smaller capillaries, enabling the tampon prepared from the absorbent composite to have a portion which will tend to rapidly draw fluid into the tampon structure, and which will tend to hold the fluid drawn into the tampon. Similarly, each layer could have a different hydrophilicity, which will allow for differential absorption characteristic. For example, one layer may be more hydrophilic than the other layer. By providing a difference in hydrophilicity, one of the layers of the tampon may serve to hold the fluid in the other layer due to the difference in the hydrophilicity. That is, the layer which is more hydrophobic will tend to keep the absorbed fluid in the layer which is more hydrophilic. In one embodiment, the first absorbent material 101 has a first density and the second absorbent material 111 has a second density, wherein the second density is greater than the first density. As a result, the portion of the tampon containing the second layer 110 of the absorbent composite 12 will quickly draw fluid into the tampon and hold the fluid in the second layer 110, until the second layer becomes saturated. The different physical properties may be achieved by various means, including using different fiber compositions in each of the layers of the absorbent composite 12 used to make the tampon of the present invention.

Each of the absorbent first and second layers 100, 110 of the absorbent composite 12 may be prepared contain absorbent materials, in particular, fibrous absorbent materials which are conventionally used to prepare tampons. Examples of such absorbent materials include materials, such as, cellulosic fibers such as wood pulp, cotton, rayon, viscose, LYOCELL® which is from Lenzing Company of Austria, or mixtures of these or other cellulosic fibers. Natural fibers can include wool, cotton, flax, hemp and wood pulp. Wood pulps include standard softwood fluffing grade such as CR-1654 (US Alliance Pulp Mills, Coosa, Ala.). Pulp may be modified in order to enhance the inherent characteristics of the fibers and their processability. Crimping may be imparted to the fibers, e.g., by conventional means. Curl may be imparted to the fibers, e.g., by methods including chemical treatment or mechanical twisting. Curl is typically imparted before crosslinking or stiffening. Pulps may be stiffened by the use of crosslinking agents such as formaldehyde or its derivatives, glutaraldehyde, epichlorohydrin, methylated compounds such as urea or urea derivatives, dialdehydes such as maleic anhydride, non-methylated urea derivatives, citric acid or other polycarboxylic acids. Some of these agents are less preferable than others due to environmental and health concerns. Pulp may also be stiffened by the use of heat or caustic treatments such as mercerization. Examples of these types of fibers include NHB416 which is a chemically crosslinked southern softwood pulp fibers which enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc of Memphis, Tenn., has a chemical treatment that sets in a curl and twist, in addition to imparting added dry and wet stiffness and resilience to the fiber. Another suitable pulp is Buckeye HP2 pulp and still another is IP Supersoft from International Paper Corporation.

For the cellulosic fiber (e.g., viscose, rayon, etc.), the fibers should have a staple length of between about 5 mm to about 35 mm. The fibers should have a denier of between about 2 to about 6. Denier is a unit of fineness of yarn based on a standard of 50 milligrams (mg) for 450 meters of yarn. The fibers can have a circular, a bi-lobal, a tri-lobal cross-sectional configuration, or some other cross-sectional configuration known to those skilled in the art. The bi-lobal configuration has a cross-sectional profile which looks like a dog bone while the tri-lobal configuration has a cross-sectional profile which looks like a "Y". The fibers can also be bleached, if desired.

When cotton fibers are used, the cotton fibers should have a staple length of between about 5 millimeters (mm) to about 30 mm. The cotton fibers should generally have a fiber size of between about 150 microns to about 280 microns. The cotton fibers can also be bleached if desired. Bleaching will make the cotton fibers whiter in appearance.

In addition to the above absorbent fibers, each of the layers 100, 110 of the absorbent composite 12 may optionally contain other fibers, which are known in the art as binder fibers. Binder fibers typically have a fiber component which will melt or fuse to other fibers in each absorbent layer. Binder fibers may be natural fibers or synthetic fibers. Synthetic fibers include those made from polyolefins, polyamides, polyesters, rayon, acrylics, viscose, superabsorbents, LYOCELL® regenerated cellulose and any other suitable synthetic fibers known to those skilled in the art. Many polyolefins are available for fiber production, for example polyethylenes such as Dow Chemical's ASPUN®) 6811A linear low density polyethylene, 2553 LLDPE and 25355 and 12350 high density polyethylene are such suitable polymers. The polyethylenes have melt flow rates, respectively, of about 26, 40, 25 and 12. Fiber forming polypropylenes include Exxon Chemical Company's ESCORENE® PD 3445 polypropylene and Montell Chemical Co.'s PF304. Another fiber could be a bi-component polyester sheath and polyethylene core and known as T255 made by Trevira of Germany. Other polyolefins are also available. Suitable rayon fibers are 1.5 denier Merge 18453 fibers from Acordis Cellulose Fibers Incorporated of Axis, Ala. The fibers can be treated by conventional compositions and/or processes to enable or enhance wettability.

In the present invention, each layer of the absorbent composite 12 may be formed from cellulosic fibers, such as cotton and rayon. As an example, the absorbent fibers can be 100% cotton, 100% rayon, or a blend of cotton and rayon fibers. Some blends which have been tried and work well include a blend of about 15% cotton to about 85% rayon; about 70% cotton to about 30% rayon; about 60% cotton to about 40% rayon; about 25% cotton to about 75% rayon; and about 6% cotton to about 94% rayon. The particular blend of fibers can vary depending upon preference. It is also possible to add polyester or other synthetic fibers to the blend to add resilient features or bondabililty to the layer of the absorbent composite.

In one embodiment of the present invention, at least one of the absorbent layer 100, 110 of the absorbent composite 12 may be a blend of viscose and binder fibers. Some blends which are believed to work well include a blend of about 70% viscose to about 95% viscose with the remainder about 30% binder fiber to about 5% binder fiber; and more advantageously about 85-90% viscose and the remainder about 15-10% binder fiber. The particular blend of fibers can vary depending upon one's preference in combination with also achieving the features of the invention.

Various methods know to those skilled in the art can be used to prepare each of the layers of the absorbent composite. Know methods such as airlaying, carding, wetlaying, hydroentangling and other known methods may be used to form the individual absorbent layers of the absorbent composite. In one embodiment of the present invention, at least one of the layers 100 or 110 is prepared using an airlaying process, wherein the airlaid fibers contain a first fiber and a second fiber, wherein the first fiber is a binder fiber and the second fiber is an absorbent fiber.

In the present invention, the first absorbent layer 100 may be prepared from any of the absorbent materials described above. The first layer 110 may be prepared using a carding process, an airlaying process of any other process know to those skilled in the art. The first absorbent layer may or may not contain binder fibers. In one embodiment of the present invention the first absorbent layer is prepared from a conventional ribbon of an absorbent material which is currently used in tampon productions. As an example, the first layer may be prepared form a carded web of airlaid web of cotton, rayon or a mixture thereof, with or without the presence of binder fibers.

In one embodiment of the present invention, the second layer is prepared from a mixture of the one or more of the absorbent fibers described above and a binder fiber. One exemplary material which may be used in the second layer of the present invention is described in patent application PCT/EP2004/006441 titled: "Airlaid Process With Improved Throughput", filed Jun. 16, 2003, published Dec. 29, 2004 as WO2004/113608, which is owned by the same assignee as this application and is incorporated herein by reference. Other airlaid materials known to those skilled in the art may also be used.

Referring back to FIG. 1, in a second embodiment of the present invention, the second layer 110 may be coextensive with the first layer 100 (not shown) or the second layer 110 may be have a smaller width and/or length than the first layer 100. As is shown in FIG. 1, the first layer has a first length $L_1$ and a first width $W_1$. The second layer 110 has a second length $L_2$ and a second width $W_2$. The first length $L_1$ may be the same length as the second length $L_2$ or, in the alternative, the first length $L_1$ may be greater than the second length $L_2$. By adjusting the length $L_2$ of the second layer 110 in relation to the length $L_1$ of the first layer 100, the properties of the resulting tampon may be adjusted to suit the needs of users. Examples of such properties which can be adjust include, for example, absorption rate, radial expansion and the like.

In a similar manner, the first width $W_1$ of the first layer 100 may be the same as the second width $W_2$ of the second layer 110 as is shown in FIG. 1. In the alternative, as is shown in FIG. 2 the first width $W_1$ of the first layer 100 may be greater than the second width $W_2$ of the second layer 110. As with the length, by adjusting the width $W_2$ of the second layer 110 in relation to the width $W_1$ of the first layer 100, the properties of the resulting tampon may be adjusted to suit the needs of users. Examples of such properties which can be adjust include, for example, absorption rate, radial expansion and the like.

In another embodiment of the present invention, the second layer 110 is located adjacent the first layer such that the second layer will located in the central portion of the tampon, when the absorbent composite is rolled and compressed. In this regard, attention is directed to FIG. 7 which shows the second layer of the composite located at the central portion 11 of the insertion end 14 of the tampon 10. In alternative embodiments, the second layer of the composite located at the central portion 11 of the trailing end 16 of the tampon 10. To ensure that the second layer is located near the central portion of the resulting tampon, the second layer is placed on the central region of the first layer. By "central region", it is intended mean the area adjacent a center line 120 of the first layer 100. The center region does not need to the exact center of the first layer, but can be located about generally around the actual center line. The center region of the first layer 100 being a position along the first length $L_1$ which is a distance $L_3$ that is about 0.35 to about 0.65 times the first length $L_1$, as measured from either longitudinal end 122 or 122' of the first absorbent layer 110. As shown in FIGS. 1 and 2, and the second layer 110 of the absorbent composite 12 is positioned on the first layer 100 such that the second layer 110 contacts said central region or on the actual center line 120 of the first layer 100.

Another way to ensure that the resulting tampon has the second layer of the absorbent composite in the central region of the tampon is when the absorbent composite is radially wound, the second layer of the absorbent composite is located in the area of the absorbent composite which is the central axis in which absorbent composite is wound. Stated another way, the second layer is located on the first layer at a location in which the composite is radially wound.

In another embodiment of the present invention, when first layer 100 has a width $W_1$ which is greater than the width $W_2$ of the second layer 110, the second layer 110 may be located at one of the longitudinal side edges 123 or 124 of the first layer 100. As is shown in FIG. 2, the first longitudinal side edge 123 and the second longitudinal side edge 124 are on opposite sides of the first layer 100. As will be discussed further, one of the longitudinal side edges will become the insertion end of the tampon and the other will become the trailing end of the tampon. Generally, for purposes of discussion herein, the first longitudinal edge 123 will become the insertion end of the tampon and the second longitudinal edge will become the trailing end.

As is show in FIGS. 1 and 2, the second layer 110 is positioned on top of the first layer 100. In the alternative embodiment of the present invention, the second layer 110 may be inset into the first layer 100, as is shown in FIG. 3.

In addition to the two layers 100 and 110, the absorbent composite may also be provided with a cover material. The cover prevents the fibers from the absorbent composite of the tampon from directly contacting the inner walls of a woman's vagina. This assures that no fibers will be left behind in the vagina after the tampon 10 is removed. The cover can be tucked into ends of the body of the tampon so as to completely surround and enclose the fibers. The cover can also be constructed from a heat-sealable material to assist in bonding it to the fibers, such as by heat and/or pressure. The cover can be formed from a nonwoven material such as a polyolefin, particularly polypropylene or polyethylene. A suitable material is a spunbond material. Suitable methods and materials for the production of tampons are well known to those skilled in the art.

Referring now to FIGS. 4, 5 and 6, the absorbent composite 12 with its first absorbent layer 100 and the second absorbent layer 110 has a liquid-permeable cover 130 placed thereon. The cover 130 will have a first major surface 131 and can be formed as a rectangular sheet, as shown. The cover 130 has a length and a width which are sized so that the cover 130 can wrap completely around the outer periphery of the absorbent composite 12, when the absorbent composite is rolled, as is shown in FIG. 5. 14. Preferably, the cover 130 will have a length which is equal to or greater than the circumference of the rolled absorbent composite before compression and will have a width which is about equal to or greater than the outside periphery of the rolled absorbent composite. By so sizing the width of the cover 130, the cover 130 will be able to wrap completely around the outer exterior surface of the absorbent composite and be overlapped upon itself in the overlap region 131 (see FIG. 5).

The liquid-permeable cover 130 can be bonded along the entire length of the overlap region 131 by using an impulse sealer or some other type of sealing mechanism. Alternatively, the cover 130 can be spot bonded at spaced apart points along the overlap region 131, if desired. The cover 130 can be bonded to either itself and/or to the absorbent composite 12 using heat, pressure, heat and pressure, ultrasonic, adhesives, glue, or any other known bonding technique. As shown in FIGS. 4 and 5, the cover 130 is adhesively bonded with an adhesive 132.

The liquid-permeable cover 130 can be formed from woven or nonwoven material having a porous substrate. Woven material includes textile fabrics which can be made from rayon, cotton, polyolefins or other synthetic yarns. The synthetics can be either staple or continuous filaments. The cover 130 may be a 12-33 gsm polypropylene spunbond. The nonwoven materials can include spunbond, bonded carded webs and hydro entangled webs. Spunbond and bonded carded webs are commercially sold by Kimberly-Clark Corporation, having an office located at 401 North Lake Street, Neenah, Wis. 54956. Another nonwoven material which can be used as the cover 16 is formed from 100 percent polyester fibers held together by a binder. This material is known as powder-bonded-carded web (PBCW). PBCW is commercially available from HDK Industries, Inc. having an office at 304 Arcadia Drive, Greenville, S.C. 29609. The cover 16 can further be formed from an apertured thermoplastic film having either a two-dimensional or a three-dimensional thickness. Apertured thermoplastic films are available from several commercial vendors including Pantex Sri, Pantex Sud srl, Via Terracini snc, having an office at 51031 Agliana, Pistoia, Italy and Applied Extrusion Technology having a mailing address of P.O. Box 582, Middleton, Del. 19709.

The liquid-permeable cover 130 can be treated with an aqueous solution to reduce frictional drag, to enhance the tampon's wettability and to enhance the ease of insertion into and withdrawal from a woman's vagina. The cover 130 can be treated either before being rolled up with the absorbent composite 12 or after the cover 130 has been positioned about the exterior surface of the absorbent composite. The different types of aqueous solutions which can be used are known to those skilled in the art. One particular type of aqueous solution is taught in U.S. Pat. No. 5,533,990 entitled "TAMPON EXHIBITING LOW FRICTIONAL DRAG." This patent is assigned to Kimberly-Clark Worldwide, Inc. and is incorporated by reference and made a part hereof.

The tampon 10 further includes a withdrawal string 38 for assisting in removing the tampon 10 from the woman's vagina. The withdrawal string 38 is attached to the absorbent material 12, and preferably, to the first and second ends, 14 and 16 respectively, of the material 12. One method of attaching the withdrawal string 38 is to form an aperture or hole through the absorbent sheet or ribbon. The withdrawal string 38 is then threaded through the aperture and looped upon itself so as to cinch it secure to the absorbent 12. The free ends of the withdrawal string 38 are then tied in a knot 40 to assure that the withdrawal string 38 will not separate from the material 12. The knot 40 also serves to prevent fraying of the withdrawal string 38 and to provide a place or point where a woman can grasp the withdrawal string 38 when she is ready to remove the tampon 10 from her vagina. It should be noted that the withdrawal string 38 holds the first and second ends, 14 and 16 respectively, in direct contact with one another and may, but need not, limit the amount they can expand while positioned within the woman's vagina. It should be noted that the withdrawal string 38 can be secured to and/or attached to various areas of the tampon 10 and can pass through the absorbent 12. The withdrawal string 38 can also be attached either before the mass of absorbent material 12 is compressed or after it is formed into the tampon.

The withdrawal string 38 can be constructed from various types of threads or ribbons. A thread or ribbon may be made from 100 percent cotton fibers and/or other materials in whole or part. The string may be bonded to the material 12, with or without tying (e.g., using one or more of the ways as for making the pre-determined pattern in material 12) to material 12 before or as material 12 is being formed into the generally cylindrical shape. In this way, there is no need (or less need) for tying the string to the tampon and better assurance that the string will stay in place and attached to the tampon before, during use and during withdrawal of the tampon till it is ready for disposal. Advantageously (though not required because the bonding characteristics of the first type of fibers in the material 12 can be sufficient), and as with the material 12, the string 38 may include bondable material, e.g., the same type of material compositions as for the material 12 or those with similar bonding characteristics. As such, the string may be a plurality of string fibers including at least a first type of string fiber being bondable to adjacent fibers and where the string is autogenous bonded with the mass of absorbent material.

The withdrawal string 38 should have a length which extends beyond the end of the tampon 10 from between about 2 inches to about 8 inches (about 51 mm to about 203 mm), preferably from about 4 inches to about 6 inches (about 102 mm to 152 mm), and most preferably, about 5 inches (about 127 mm). The withdrawal string 38 can be dyed and/or treated with an anti-wicking agent, such as wax, before being secured to the material 12. The anti-wicking agent will facilitate and prevent body fluids from wicking along the withdrawal string 38 and contacting the inner surface of a woman's undergarment. A dry, clean withdrawal string 38 is preferred by the user, especially when she goes to remove the tampon 10 from her vagina.

Depending upon the desired absorbency one desires in the finished tampon, the basis weight of the absorbent sheet can vary. The U. S. Food and Drug Administration (FDA) has set absorbency standards for "junior", "regular", "super", "super-plus" and "super-plus-plus" size tampons. In order to meet the certain standards for these sizes, the absorbent sheets are targeted to have basis weights of about 100 grams per square meter (gsm), 120-150 gsm, 170-180 gsm, 210-230 gsm, and 240-260 gsm, respectively, and as much as 270-290 gsm. Typically, the formation process is controlled to produce an absorbent sheet with a width of between about 40 mm to about 60 mm, preferably about 50 mm. The basis weight and/or the length of the tampon 10 can also be adjusted to form the different size tampons. Typically, the length of the first absorbent layer can vary between about 100 mm and about 200 mm, depending on the required absorbency and basis weight.

To prepare the tampon of the present invention, the following method may be used. Generally, first is provided first absorbent material 101. Next, a second absorbent material 111 is provided. The second absorbent material 111 is place on the first absorbent material to form and absorbent composite 12. Next, the absorbent composite may optionally provided with a cover 130 described above. Once the absorbent composite is formed the absorbent composite is formed into a generally cylindrical shape, which a method known to those skilled in the art, such as radially winding the absorbent composite (shown in FIGS. 4, 5 and 6) or folding the absorbent composite. To radially wind the absorbent composite, a spindle 190 is placed on both sides of the absorbent composite 12. The spindle 190 is rotated in a direction 191 to form a softwind 140, as is shown in FIGS. 5 and 6. Once the absorbent composite is formed in to a generally cylindrical shape, the absorbent composite is compressed to increase the density of the absorbent composite, thereby forming the tampon.

As is discussed above, the tampon may be provided with a withdrawal sting 38. The string may be placed around the absorbent composite prior to forming the generally cylindrical shape, as shown in FIGS. 4, 5 and 6, or the other methods described above, or the withdrawal string may be attached after rolling, using one or more of the methods described above.

Figure 8:
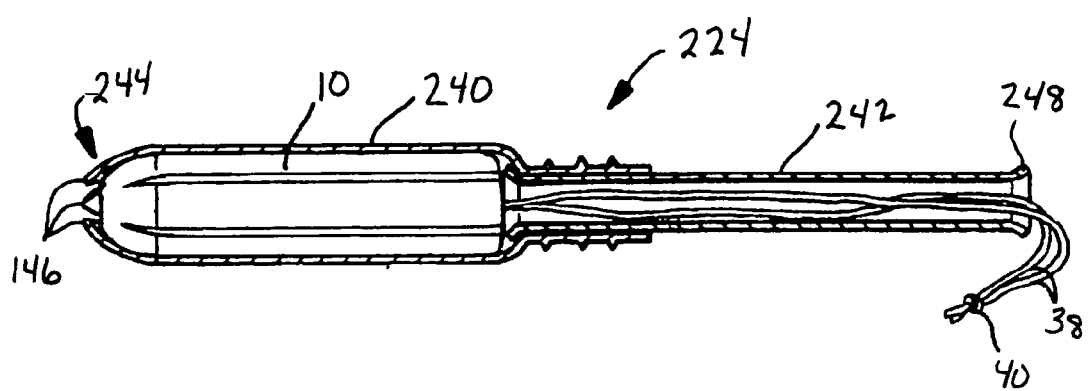
FIG. 8 shows a cross-section view of a tampon applicator which may be used in the present invention.

As illustrated in FIG. 8, the tampon applicator 224, which is used to insert the tampon 10 into a woman's vagina, comprises an outer tube 240 and an inner tube 242. The outer tube 240 is sized and shaped to house the tampon 10. A portion of the outer tube 240 is partially broken away in FIG. 8 to illustrate the tampon 10. In the illustrated embodiment, the outer tube 240 has a substantially smooth exterior surface, which facilitates insertion of the tampon applicator 224, and thus the tampon 10, into a woman's vagina. When the surface of the exterior layer is smooth and/or slippery, the outer tube 240 will easily slide into a woman's vagina without subjecting the internal tissues of the woman's vagina to abrasion. The outer tube 240 may be coated to give it a high slip characteristic. Wax, polyethylene, a combination of wax and polyethylene, cellophane, and clay are representative coatings that can be applied to the exterior layer to facilitate comfortable insertion. The illustrated outer tube 240 is a straight, elongated cylindrical tube. It is understood however that the applicator 224 could have different shapes and sizes than those illustrated and described herein.

Extending outwardly from the outer tube is an insertion tip 244. The insertion tip 244, which is formed as one-piece with the outer tube 240, may be dome-shaped to facilitate insertion of the outer tube into a woman's vagina in a comfortable manner. The illustrated insertion tip 244 is made of a thin, flexible material and has a plurality of soft, flexible petals 146 that are arranged to form the dome-shape. The petals 146 are capable of radially flexing (i.e., bending outward) to provide an enlarged opening through which the tampon 10 can exit when it is pushed forward by the inner tube 242. In an alternative configuration, the outer tube may have an abrupt ending without an applicator tip or petals. For example, some cardboard applicators do not have an applicator tip, but may have a film cover or be completely open.

The inner tube 242 is an elongate cylinder that is used to engage the tampon 10 contained in the outer tube 240. A free end 248 of the inner tube 242 is configured for digital manipulation by the user's forefinger so that the user can move the inner tube with respect to the outer tube 240. In other words, the free end 248 functions as a grip for the forefinger of the user. It is also possible to form an enlarged ring or flange on the distal end of the inner tube 242 to provide for a larger contact surface for the user's forefinger.

The inner tube 242 is used to push the tampon 10 out of the outer tube 240 and into the woman's vagina by telescopically moving into the outer tube. As the inner tube 242 is pushed into the outer tube 240 by the user, the tampon 10 is forced forward against the insertion tip 244. The contact by the tampon 10 causes the petals 146 of the insertion tip 244 to radially open to a diameter sufficient to allow the tampon to exit the outer tube 240 and into the woman's vagina. With the tampon 10 properly positioned in the woman's vagina, the tampon applicator 224 is withdrawn. In a used configuration of the tampon applicator 224, the inner tube 242 is received in the outer tube 240. As a result, the used configuration of the tampon applicator 224 has a length that is substantially equal to a length of the outer tube 240.

The inner tube 242, the outer tube 240, and the insertion tip 244 can be formed from any suitable material including, but not limited to, paper, paperboard, cardboard, plastic, thermoplastic film, or a combination thereof. If paper, paperboard, or cardboard is used, it can be coated with a wax or water-insoluble polymer to render it water-resistant. Suitable plastic materials include polyolefins, such as low density polyethylene and low density polypropylene. Construction and operation of the tampon applicator described heretofore is conventional and known to those skilled in the art.

Test Methods

The testing set forth herein is performed where the tampons to be tested are conditioned 24 hours and tested under TAPPI standard conditions of 23±1° C. and 50±2% RH. The test equipment discussed is exemplary and should be used to conduct the testing, however, alternative equipment that is equivalent in all material respects for the given test can be used also (but in the event of conflict between test results the test results from the exemplary equipment shall control).

Radial Expansion Test

After conditioning 10 sample tampons per above, each is treated as follows. Weigh 1000 mL (replenish as needed to be able to saturate all tampons tested) of commercially available saline solution (sodium chloride), 0.9+/−0.005% (w/w) aqueous isotonic saline and pour into a wide mouth beaker capable of holding at least 1500 mL. Drop the sample into the solution and allow to remain there for at least 60 seconds (and no more than 10 minutes) in order to reach saturation capacity (carefully push sample under the surface of the solution if necessary to help begin absorption). Delicately remove the sample being careful to not compress the sample any more than needed to get it to the diameter measuring equipment per the Diameter Measurement Procedure hereafter (in this regard, it is recommended that the visibly smallest diameter portion of the sample be carefully grasped to remove the sample from the solution and get it to the diameter measuring equipment). After removing the sample, hold above the solution beaker for about 2 minutes to allow unabsorbed solution to drip back into the beaker. After the 2 minutes, proceed immediately to the diameter measuring equipment and determine the diameter of the sample using the Diameter Measurement Procedure. Ten samples are tested in this manner and the diameter of each zone for each sample is added together and the collective total diameter for that zone divided by 10, which thereby determines the Diameter, of the respective first or second zone, of the tampon which is discussed herein and set forth in the claims.

Diameter Measurement Procedure

The diameter of an absorbent tampon of the invention is found using the Compression Tester model KES-FB-2 manufactured by Kato Tech Co., Ltd in Japan. The diameter of a sample is found by a single cycle compression of the sample between two circular stainless steel plungers of a tip area of 2 mm$^2$ with a surface measuring 1 mm by 2 mm, for each. The velocity of compression is 1 mm/sec. When the pressure attains a level of 1.0 grams force/cm$^2$ (gf/cm$^2$) the top plunger retracts at the same velocity of 1 mm/sec. The diameter is taken during the compression of the sample at the pressure of 0.5 gf/cm$^2$ as the plungers first move towards each other. This test is first conducted on the first zone (i.e., the one having a diameter corresponding to the generally cylindrical shape) at its visibly narrowest diameter on the sample by placing that spot at the center of the test plunger (i.e., and the plungers having a sufficient spacer attached to their surfaces to avoid compressing the second zone during this part of the measurement), and then operating the test equipment to so measure. After the diameter of the first zone is measured, then the diameter of the second zone (i.e., the one having a diameter corresponding to generally non-cylindrical shape) at its visibly widest diameter on the sample, is measured for that same sample by placing that spot at the center of the test plunger (i.e., and the plungers having the spacer removed so they have a completely smooth surface), and then operating the test equipment to so measure. The diameter of each zone is measured to the closest hundredth of a millimeter for each sample.

All publications, patents, and patent documents cited in the specification are incorporated by reference herein, as though individually incorporated by reference. In the case of any inconsistencies, the present disclosure, including any definitions herein, will prevail. While the invention has been described in detail with respect to the specific aspects thereof, it will be appreciated that those skilled in the art, upon attaining an understanding of the foregoing, may readily conceive of alterations to, variations of, and equivalents to these aspects which fall within the spirit and scope of the present invention, which should be assessed accordingly to that of the appended claims.

What is claimed is:

1. An absorbent tampon comprising:
   a mass of an absorbent composite radially compressed into a generally cylindrical shape, said absorbent composite comprises a first layer and a second layer, wherein, when the absorbent composite is in an uncompressed configuration, the second layer is positioned in a facing relationship on top of the first layer, said first layer comprises a first absorbent material having a first density and said second layer comprises a second absorbent material having a second density and the second density has a value which is greater than the first density, and wherein the first absorbent material and the second absorbent material comprise one of wood pulp, cotton, rayon, viscose, wool, flax, or hemp and the second layer further comprises a binder fiber melted or fused to absorbent fibers, and wherein the first layer has a first length, a first width, a first longitudinal side edge and a second longitudinal side edge, and the second layer has a second length and a second width, and the first length is greater than the second length and the first width is the same as the second width such that the second layer extends from the first longitudinal side edge of the first layer to the second longitudinal side edge of the first layer, and wherein the first layer has a central region located at a position along the first length which is about one-half a distance of the first length as measured from a longitudinal end of the first layer and the second layer is positioned on the first layer such that the second layer contacts at least a portion of the central region of the first layer, and wherein when the absorbent composite is in a radially compressed configuration, a portion of the second layer is in a facing relationship with another portion of the same second layer;
   a cover that at least partially surrounds the absorbent composite, and an insertion end and a trailing end, wherein the insertion end is formed from the first longitudinal side edge and the trailing end is formed from the second longitudinal side edge.

2. The absorbent tampon according to claim 1, wherein the second layer has a different fluid intake rate compared to the first layer.

3. The absorbent tampon according to claim 2, wherein the second layer has a faster intake rate compared to the first layer.

4. The absorbent tampon according to claim 1, further comprising a withdraw means extending from the trailing end to allow a user to remove the tampon after use.

5. The absorbent tampon according to claim 4, wherein the withdraw means comprises a withdraw string.

6. The absorbent tampon according to claim 1, wherein the second layer comprises an airlaid material.

7. The absorbent tampon according to claim 1, wherein the first layer comprises a carded web or an airlaid web and the second layer comprises an airlaid web.

* * * * *